(12) United States Patent
Dumanli Oktar (10) Patent No.: US 10,149,636 B2
(45) Date of Patent: Dec. 11, 2018

(54) RELAY DEVICE FOR RELAYING RADIO FREQUENCY SIGNALS RECEIVED FROM AN ANTENNA IMPLANTED WITHIN A PATIENT'S BODY TO ANOTHER DEVICE

(71) Applicant: KABUSHIKI KAISHA TOSHIBA, Tokyo (JP)

(72) Inventor: Sema Dumanli Oktar, Bristol (GB)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 15/507,541

(22) PCT Filed: Mar. 20, 2015

(86) PCT No.: PCT/GB2015/050844
§ 371 (c)(1),
(2) Date: Feb. 28, 2017

(87) PCT Pub. No.: WO2016/151274
PCT Pub. Date: Sep. 29, 2016

(65) Prior Publication Data
US 2018/0228397 A1    Aug. 16, 2018

(51) Int. Cl.
| H01Q 1/12 | (2006.01) |
| H01Q 1/27 | (2006.01) |
| A61B 5/07 | (2006.01) |
| A61N 1/372 | (2006.01) |
| H01Q 13/18 | (2006.01) |

(Continued)

(52) U.S. Cl.
CPC ............ *A61B 5/076* (2013.01); *A61B 5/4851* (2013.01); *A61B 5/686* (2013.01); *A61F 2/32* (2013.01); *A61N 1/37229* (2013.01); *H01Q 1/273* (2013.01); *H01Q 5/371* (2015.01); *H01Q 13/18* (2013.01); *A61F 2002/3067* (2013.01); *A61N 1/362* (2013.01)

(58) Field of Classification Search
None
See application file for complete search history.

(56) References Cited

U.S. PATENT DOCUMENTS 7,486,184 B2 * 2/2009 Dougherty ............... H01Q 1/22
128/903
8,209,018 B2 * 6/2012 Osorio ................. A61B 5/4094
607/45

(Continued)

*Primary Examiner* — Tuan A Tran
(74) *Attorney, Agent, or Firm* — Finnegan, Henderson, Farabow, Garrett & Dunner, L.L.P.

(57) ABSTRACT

A relay device (201) is described for relaying radio frequency signals received from an antenna implanted within a patient's body to another device located outside the patient's body, the relay device comprising a first slot antenna for detecting radio frequency signals sent from the antenna implanted within the patient's body and a second slot antenna for transmitting radio frequency signals to the other device located outside the patient's body, whereby the first and second slot antennas comprise elongated slots (209, 211) on opposite sides of a cavity (203). The signals to be transmitted by the second slot antenna are to be used to relay information conveyed by the signals detected by the first slot antenna. The relay device also comprises switching means (215, 217) for switching the first and second slot antennas between active and inactive configurations.

17 Claims, 6 Drawing Sheets

(51) Int. Cl.
*H01Q 5/371* (2015.01)
*A61B 5/00* (2006.01)
*A61F 2/32* (2006.01)
A61F 2/30 (2006.01)
A61N 1/362 (2006.01)

(56) References Cited

U.S. PATENT DOCUMENTS

| | | | | |
|---|---|---|---|---|
| 8,519,901 | B2* | 8/2013 | Tu | H01Q 3/24 |
| | | | | 343/769 |
| 8,611,990 | B2* | 12/2013 | Richardson | A61B 5/0006 |
| | | | | 600/508 |
| 8,798,728 | B2* | 8/2014 | Drew | A61B 5/0006 |
| | | | | 600/509 |
| 8,939,905 | B2* | 1/2015 | Schugt | A61B 5/686 |
| | | | | 600/302 |
| 8,983,615 | B2* | 3/2015 | Tahmasian | A61N 1/37217 |
| | | | | 607/59 |
| 9,002,456 | B2* | 4/2015 | Goossen | A61N 1/3718 |
| | | | | 607/32 |
| 9,114,260 | B2* | 8/2015 | Pless | A61N 1/36071 |
| 9,259,177 | B2* | 2/2016 | Drew | A61B 5/0006 |
| 9,831,544 | B2* | 11/2017 | Choi | H01Q 5/364 |

* cited by examiner

RELAY DEVICE FOR RELAYING RADIO FREQUENCY SIGNALS RECEIVED FROM AN ANTENNA IMPLANTED WITHIN A PATIENT'S BODY TO ANOTHER DEVICE

FIELD

Embodiments described herein relate to a relay device for relaying radio frequency signals received from an antenna implanted within a patient's body to another device located outside the patient's body.

BACKGROUND

Smart implants are increasingly recognised for use in surgical procedures on patients. Typically, a smart implant (which may be, for example, an orthopaedic implant used to replace or support damaged tissue or bone) includes sensors for sensing the environment surrounding the implant and a transmitter for wirelessly transmitting data reporting on the environment to an external receiver located outside the body. Using the wireless link, the implant can send data out at certain intervals or provide real-time feedback, such that a medical practitioner is able to monitor the status of the implant and/or conditions within the patient's body.

The wireless link between the implant and the external receiver may be difficult to secure due to the fact that electromagnetic waves quickly attenuate as they propagate through human tissue. Depending on the depth of the implant within the body, the signal strength may be quite weak by the time the waves reach the skin. In order to address this problem, relay devices have been developed that are designed to be worn on the outside of the patient's body, or carried close thereto, and which can detect the signals emanating from the implant and relay those signals over the distance from the patient's body to the external receiver. Such "on-body relay devices" may comprise one or more antennas for relaying the signals between the implant and the external receiver.

There is a continuing need to improve on-body relay devices for relaying signals from a smart implant to an external receiver located outside the patient's body.

BRIEF DESCRIPTION OF DRAWINGS

Embodiments of the invention will now be described by way of example with reference to the accompanying drawings in which.

DETAILED DESCRIPTION

According to a first embodiment, there is provided a relay device for relaying radio frequency signals received from an antenna implanted within a patient's body to another device located outside the patient's body, the relay device comprising:
- a first slot antenna for detecting radio frequency signals sent from the antenna implanted within the patient's body;
- a second slot antenna for transmitting radio frequency signals to said other device located outside the patient's body, the signals transmitted by the second slot antenna being used to relay information that is conveyed within the signals detected by the first slot antenna;
- wherein the first and second slot antennas comprise elongated slots on opposite sides of a cavity;
- the relay device comprising switching means for switching the first and second slot antennas between active and inactive configurations;
- wherein, when the first slot antenna is in its active configuration, the first slot antenna is operable to detect signals in a first frequency band of the first slot antenna and when the first slot antenna is in its inactive configuration, the first slot antenna is less responsive to detecting signals in the first frequency band of the first slot antenna compared to when the first slot antenna is in its active configuration; and
- when the second slot antenna is in its active configuration, the second slot antenna is operable to transmit signals in a first frequency band of the second slot antenna and when the second slot antenna is in its inactive configuration, the second slot antenna is less effective at transmitting signals in the first frequency band of the second slot antenna compared to when the second slot antenna is in its active configuration.

In some embodiments, the switching means is configured such that when the first slot antenna is in its active configuration, the second slot antenna is in its inactive configuration and when the first slot antenna is in its inactive configuration, the second slot antenna is in its active configuration.

In some embodiments, the switching means is configured to alternately activate the first and second slot antennas.

In some embodiments, the switching means is configured to switch the first slot antenna from an active configuration to an inactive configuration by short circuiting the first slot antenna.

In some embodiments, the switching means is configured to switch the second slot antenna from an active configuration to an inactive configuration by short circuiting the second slot antenna.

In some embodiments, the switching means comprises a switch that bridges the sides of the first slot antenna and/or a switch that bridges the sides of the second slot antenna. The switch(es) may comprise RF-MEMS switches.

In some embodiments, the slots in the first and second slot antennas are oriented such that they extend lengthwise in different directions from one another. In some embodiments, the slots of the first and second slot antennas extend lengthwise perpendicularly to one another.

In some embodiments, the first and second slot antennas are both fed by a common feed. The common feed may be a stripline that passes through the cavity.

In some embodiments, the slots in the first and second slot antennas widen as each slot extends lengthwise from its centre.

In some embodiments, the width of the slots in the first and second slot antennas increases in a series of steps as each slot extends lengthwise from its centre. In some embodiments, at each step, the respective slot widens by a distance equivalent to the width of the slot at the mid-point along its length. In some embodiments, the steps in the respective slots become progressively longer as each slot extends lengthwise from its centre.

In some embodiments, the relay device is wearable by a patient. In some embodiments, the relay device has means for attaching the device to the patient's skin.

In embodiments described herein, the relay device is not only suitable for facing the skin to receive signals from the implant, but also is capable of switching its radiation pattern so that it can efficiently relay the collected data to the remote receiver device.

Figure 1:
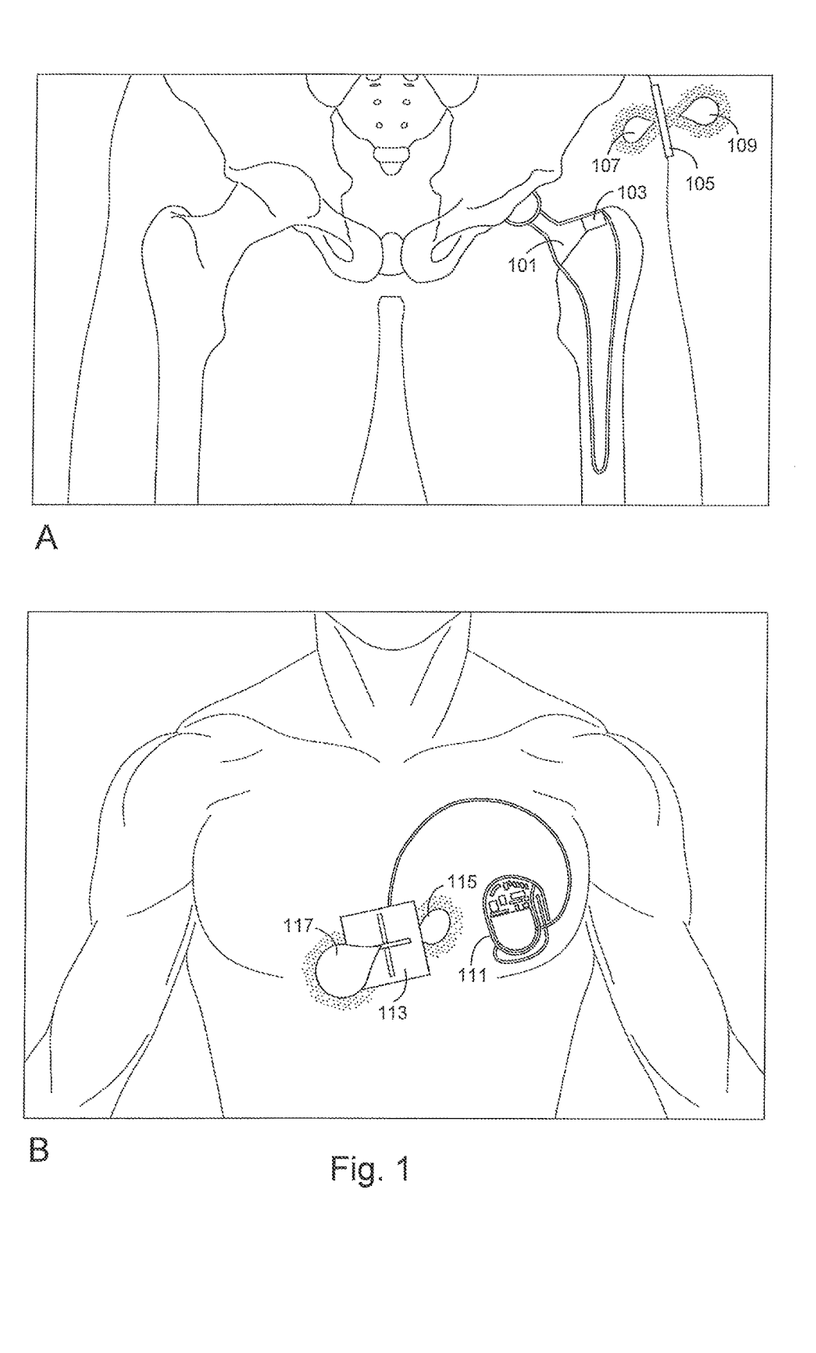
FIG. 1 shows examples of how embodiments of a relay device may be implemented.

FIG. 1 shows two examples of how embodiments of a relay device may be implemented. FIG. 1A shows an example in which a patient has an orthopaedic implant 101 in their hip. The hip implant 101 is configured to monitor the status of the implant and the surrounding tissue. The implant includes an antenna 103 that is used to transmit wireless signals from the implant to a receiving device located outside the body (the receiving device is not itself shown in FIG. 1). The wireless signals encode information about the status of the implant and/or the condition of the surrounding tissue. A physician or surgeon may use the signals received from the implant to determine the state of the implant and/or surrounding tissue.

Since the wireless signals from the implant must travel through the patient's tissue en-route to the surface of the body, the strength of those signals may be compromised by the time they reach the surface. In order to ensure the information encoded in the signals is not lost, the patient is provided with a relay device 105, which in the embodiment shown in FIG. 1a is worn on the patient's body, near to where the implant is located. The relay device 105 is configured to detect the wireless signals 107 emanating from the implant within the patient's body and to relay the information encoded in the wireless signals to the external receiving device. As can be seen, in FIG. 1A, the relay device serves to transmit the relay signals 109 away from the body, in the opposite direction from which the wireless signals 107 being sent from the implant are received.

FIG. 1B shows a similar example, in which the patient has a pacemaker 111 that is fitted with an antenna for transmitting wireless signals from the pacemaker to a receiving device located outside the body. In this example, the patient is provided with a similar relay device 113 to that shown in FIG. 1A, which is worn on the patient's chest. The relay device 113 receives the signals 115 sent from the pacemaker and transmits signals 117 relaying the information from the pacemaker to an external receiver.

FIG. 2A shows a more detailed view of a relay device according to an embodiment. As shown in FIG. 2A, the relay device 201 comprises a shallow cuboidal cavity 203 having lower and upper surfaces 205, 207, which in the present embodiment are square. The lower surface 205 comprises a first slot antenna having an elongate slot 209. The upper surface 207, which is located on the opposite side of the cavity from the first slot antenna, comprises a second slot antenna, also having an elongate slot 211. In effect, each one of the slot antennas comprises a cavity backed slot antenna, with the two slot antennas sharing the same cavity.

The slots 209, 211 in the first and second slot antennas have different orientations to one another i.e. the slots extend lengthwise in different directions from one another. In the embodiment shown in FIG. 2A, the slots are oriented perpendicularly to one another. However, it will be understood that this is by way of example only and it is not essential for the slots to be oriented at 90° to one another. The differing orientations of the slots means that the spatial pattern of radiation detected by the first slot antenna differs from the spatial pattern of radiation transmitted from the second slot antenna, helping to avoid cross-talk between signals arriving at and leaving the relay device.

A stripline 213 is used to feed the first and second slot antennas. Thus, the two antennas are fed by a common feed point. In this embodiment, the stripline 213 has first and second parts that are contiguous with one another and which extend in different directions at right angles to one another; the first part extends parallel to the first slot and crosses perpendicularly to the second slot, and the second part extends parallel to the second slot and crosses perpendicularly to the second slot.

It will be understood that the stripline 213 passes through the cavity i.e. the stripline passes through the volume defined between the upper and lower faces of the cavity. In some embodiments, the volume of the cavity may be filled with a dielectric material such that the stripline is surrounded by the dielectric material.

The slots of the first and second slot antennas are each provided with a switch 215, 217 that can be used to short circuit the respective slot antenna. In this embodiment, the switches 215, 217 are located at or close to the centre of the slots' length. By shorting the antenna, the switches effectively switch the antenna from an active configuration into an inactive configuration. The active and inactive configurations refer, respectively, to the antenna's ability to detect/transmit radio frequency waves within a predetermined band of frequencies. For example, by shorting the first slot antenna, the first slot antenna is rendered less able to detect a particular band of radio frequencies transmitted from the implant within the patient's body. By shorting the second slot antenna, the second slot antenna is rendered less able to relay signals to the exterior device using a particular band of frequencies.

FIG. 2B shows a plan view of a relay device according to another embodiment. For convenience, parts having the same function as that shown in FIG. 2A have the same reference numerals. In this embodiment, the first slot 209 is longer than the second slot 211, and narrower than the second slot. It will be understood, therefore, that the dimensions of the two slots need not be identical in embodiments discussed herein.

In some embodiments, the first and second slot antennas are designed to operate in the 2.4 GHz ISM band i.e. when in an active configuration, the first and second slot antennas may be responsive to (or operable to transmit) radio wave frequencies within the 2.4 GHz ISM band, or a first sub-band, thereof. When in an inactive configuration, the first and second slot antennas may become less responsive to/less able to transmit radio frequencies within the 2.4 GHz ISM band. Alternatively, when in the inactive configuration, the first and second slot antennas may become less responsive to/less able to transmit in the first sub-band of the 2.4 GHz ISM band, but may still be responsive to/operable to transmit in a different sub-band of the 2.4 GHz ISM band.

By activating the first and second slot antennas at different times from one another, the relay device of the present embodiment can achieve radiation pattern diversity in a way that is not possible using conventional cavity backed slot antennas; the relay device is able to alternate between detecting incoming waves from a first side of the device and transmitting waves in an outgoing direction from the other side of the device, without the need for separate feeds to the two antennas. Embodiments thereby provide re-configurability in terms of the radiation pattern which is being detected/transmitted by the relay device at any one time.

In use, the power dissipated by the antenna can be calculated by integrating the ohmic losses in the near field, these losses being caused by the conductivity of the tissues. In this respect, a slot antenna (which is an example of a magnetic antenna) provides an advantage over electric antennas, in that the electric field in the near-field of the antenna is smaller. Consequently, the use of a slot antenna in the implant and relay device can help to enhance the strength of signals detected by the relay device, since the ohmic losses in the patient's tissue will be reduced compared to the case where electric antennas are used.

It will be understood that, in terms of relaying the information received the patient's implant, the first slot antenna may be connected to a wireless transceiver (not shown in the Figures) which will demodulate the signal received from the implant by the first slot antenna and re-modulate that signal for transmission by the second slot antenna. The transceiver may also be used to drive the switches on each slot. In other embodiments, the first slot antenna may simply be connected to an amplifier, whereby the received signal is amplified before being retransmitted by the second slot antenna, without the need for data processing; this may be appropriate in cases in which the mere presence or absence of a signal from the implant provides information about the implant's status or its surroundings, rather than the signals themselves being modulated with actual data.

The function of the relay device according to an embodiment will now be described in more detail. As a starting point, the cavity and the slots are considered to be isolated. The location of each slot and the cavity resonances can be theoretically predicted (the interaction between them is ignored at this stage).

If the slot is a thin slot (i.e. the length is much greater than the width), then the lowest slot resonance, $TE_{10}$ will be primarily defined by the slot length. In the present embodiment, it will be assumed that the lengths of the slots in the first and second slot antennas are 80 mm and 70 mm, respectively. In the present embodiment, the $TE_{10}$ mode will occur approximately at 2 GHz. It is desirable to keep the width of the slots as small as possible, particularly where switches for switching between the active and inactive configurations bridge the slots (see below). At the same time, it should be noted that increasing the width of the slots will improve the 10 dB bandwidth of the input response, so a balance must be struck when selecting the slot width. In the present embodiment, the slots of the first and second slot antennas have widths of 2 mm and 1 mm, respectively, these slot widths being less than $0.02\lambda$ where $\lambda$ denotes the first resonant frequency of the cavity.

Assuming that the backing cavity is fully enclosed, the $TE_{nml}$ mode resonant frequency $f_{nml}$ can be modelled as:

$$f_{nml} = \frac{c}{\sqrt{\epsilon_r}} \sqrt{\left(\frac{l}{2d}\right)^2 + \left(\frac{m}{2b}\right)^2 + \left(\frac{n}{2a}\right)^2}$$

where c is the speed of light, $\epsilon_r$ is the relative permittivity of the substrate, a and d are the length and width of the cavity, and b is the height of the cavity. In the present embodiment, the length of the cavity is equal to the width of the cavity, whilst the cavity height is much smaller than the length and the width. If the thickness of the cavity is assumed to be 3 mm, which is less than $0.03\lambda$ where $\lambda$ is the wavelength of the first resonant frequency, and the length and width of the cavity are both assumed to be 80 mm, the $TE_{101}$ mode resonant frequency for the cavity is calculated to be around 2.8 GHz.

In practice, the actual cavity resonances will shift due to the introduction of the slots, and the slot resonance will also be affected by the cavity. Fine tuning can be performed using simulations.

The height of the cavity has a positive effect on the bandwidth of the antenna therefore it can be decreased as long as the desired band of frequencies is still covered.

Both slots are excited with the single symmetric stripline, which changes direction as it extends through the substrate. In one example, the stripline width is calculated such that its characteristic impedance is 50Ω (it can be matched to any impedance depending on the system's output impedance). On extending from the cavity edge, the stripline first encounters the slot in the second slot antenna. The stripline will typically have an offset of one quarter of the length of the slot (e.g. 0.22*slot length<feed offset<0.28*slot length), where the "offset" refers to the distance between the respective slot and the portion of the stripline that extends parallel to the length of the slot (see FIG. 2B, for example). The stripline then turns through a right angle and has the same offset at the slot in the first slot antenna. The stripline is open circuited at a distance where the input impedance seen from the feed port is 50Ω for each state of the antenna.

In an example embodiment, the distance between the point at which the footprint of the stripline crosses the slot in the second slot antenna and the point at which the stripline is open circuited is $0.3\lambda$. The position of the feed line together with the length of the feed line sets the impedance.

Figure 2:
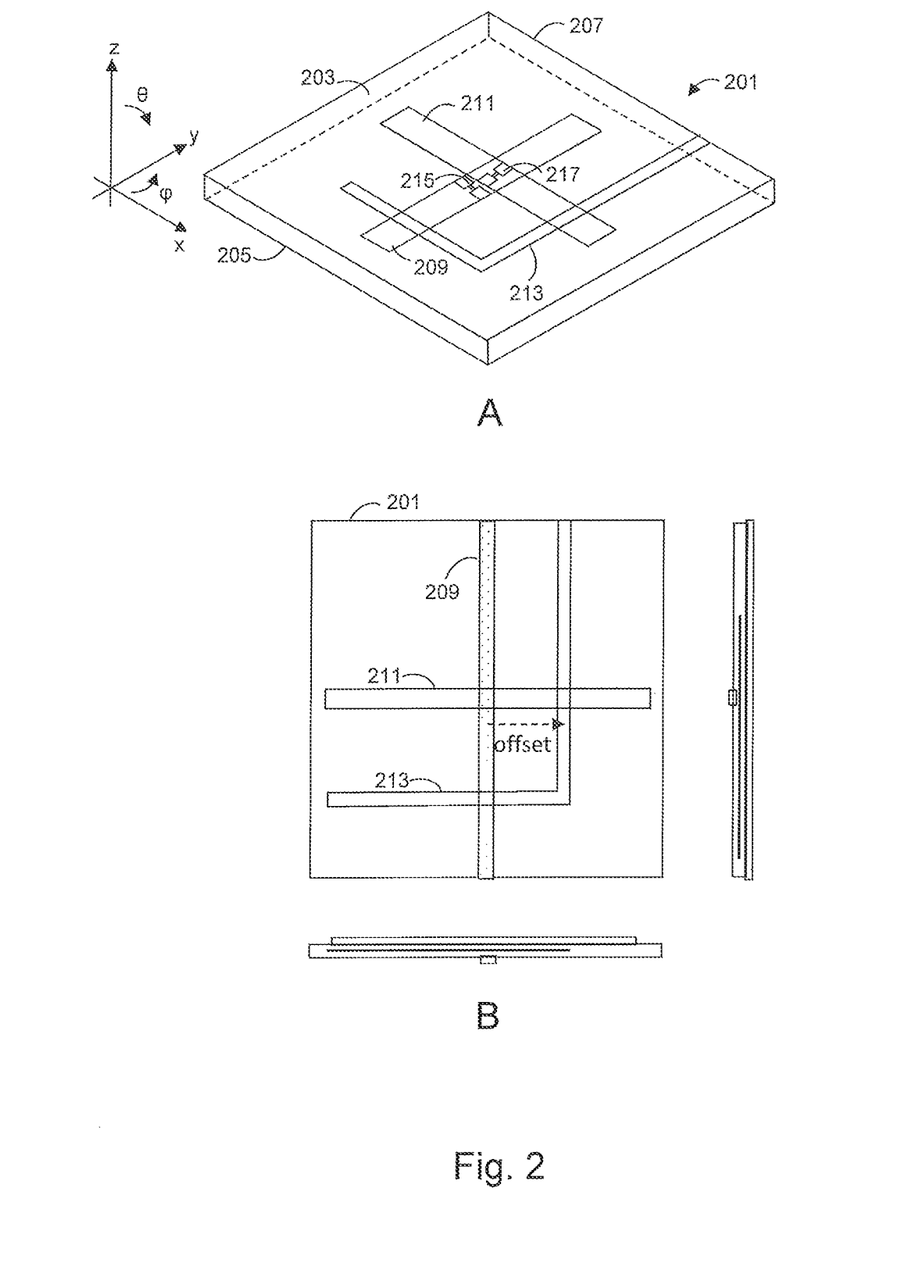
FIG. 2A shows a schematic of a relay device according to an embodiment.
FIG. 2B shows a schematic of a relay device according to another embodiment.
Figure 3:
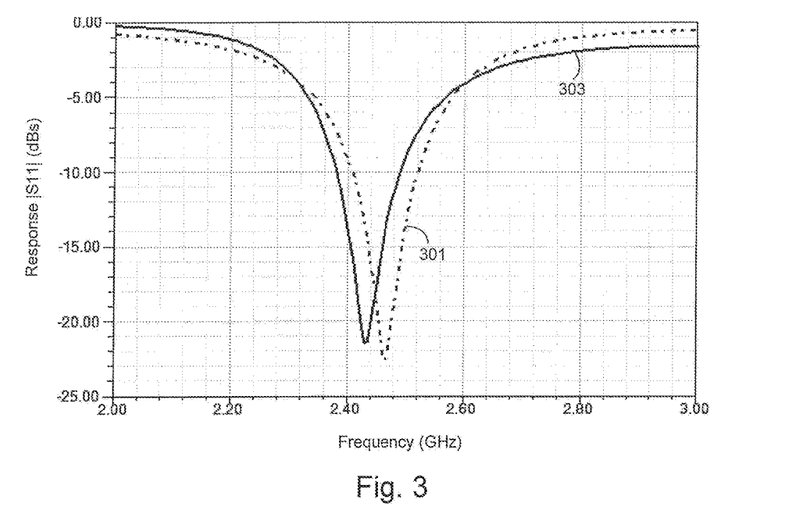
FIG. 3 shows how the frequency response of the first slot antenna varies when the second slot antenna is inactivated in a relay device according to an embodiment, and vice versa.
Figure 4:
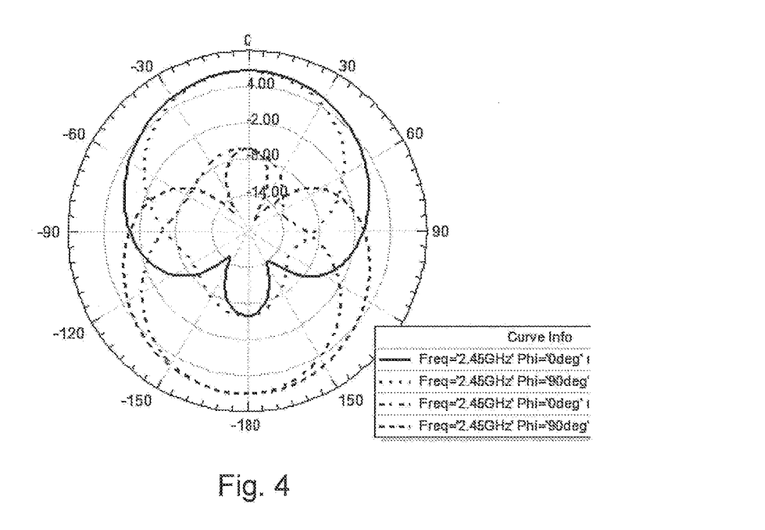
FIG. 4 shows 2D representations of the generated radiation patterns for the first and second slot antennas of a relay device according to an embodiment.

FIG. 3 shows how the frequency response of the first slot antenna varies when the second slot antenna is shorted and vice versa. The first (dotted) graph 301 shows the frequency response for the first slot antenna when the second slot antenna is shorted and the second (line) graph 303 shows the frequency response for the second slot antenna when the first slot antenna is shorted. FIG. 4 shows 2D representations of the generated radiation patterns at φ=0° and 90° while θ changes between −180 and 180. Here, θ is the elevation assuming that the main axis of the antenna lies in the horizontal (x-y) plane (see FIG. 2A).

Figure 5:
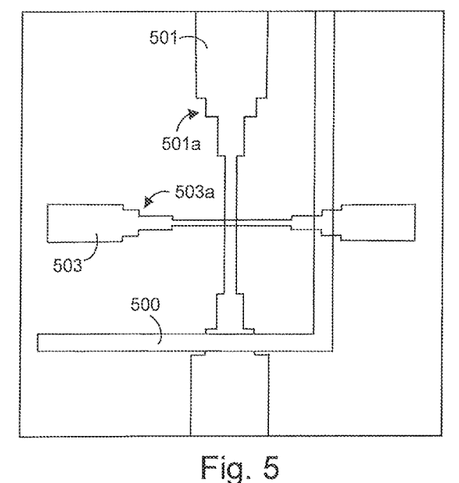
FIG. 5 shows a schematic of a relay device according to another embodiment.

FIG. 5 shows a schematic of another embodiment in which the slot antennas have a larger bandwidth than that shown in FIG. 2. An in FIG. 2, the two antennas are excited by a single feed in the form of a stripline 500.

In the embodiment of FIG. 5, the width of each slot increases as the slot extends lengthwise from its centre. As shown in FIG. 5, the width of each slot 501, 503 increases progressively in a series of steps 501a, 503a. At each step, the width of the slot increases monotonically by a factor of twice the width of the slot at the mid-point of its length. The length of each step becomes shorter as the slot becomes wider. In the present embodiment, the stair length is decreased harmonically (for example, the first step may have a length equal to half of the slot length, the second step may have a length equal to one third of the slot length and the third step may have a length equal to one quarter of the slot length).

Figure 6:
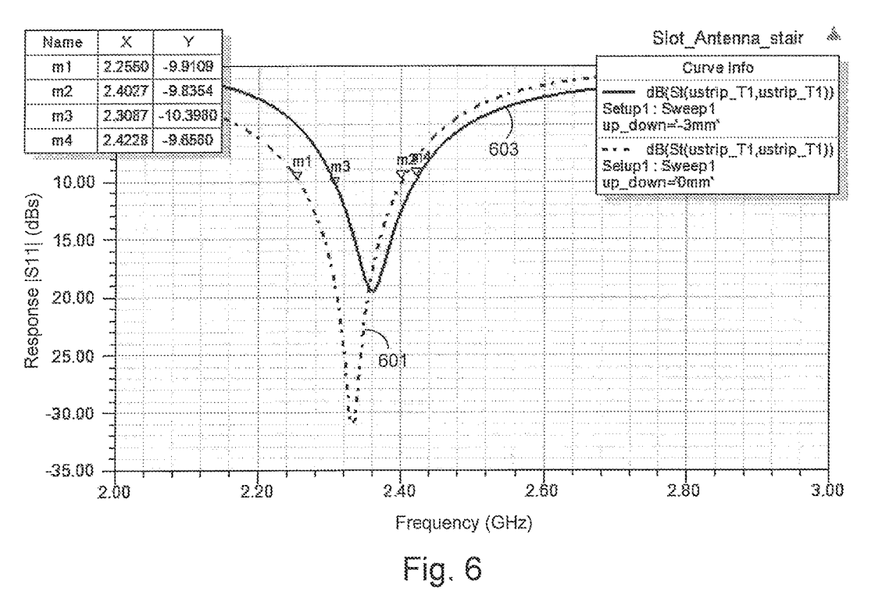
FIG. 6 shows how the frequency response of the first slot antenna varies when the second slot antenna is inactivated in the relay device of FIG. 5.

FIG. 6 shows how the frequency response of the first slot antenna for the embodiment of FIG. 5 varies in response to shorting the second slot antenna and vice versa. The first (dotted) graph 601 shows the frequency response for the first slot antenna when the second slot antenna is shorted and the second (line) graph 603 shows the frequency response for the second slot antenna when the first slot antenna is shorted.

Figure 7:
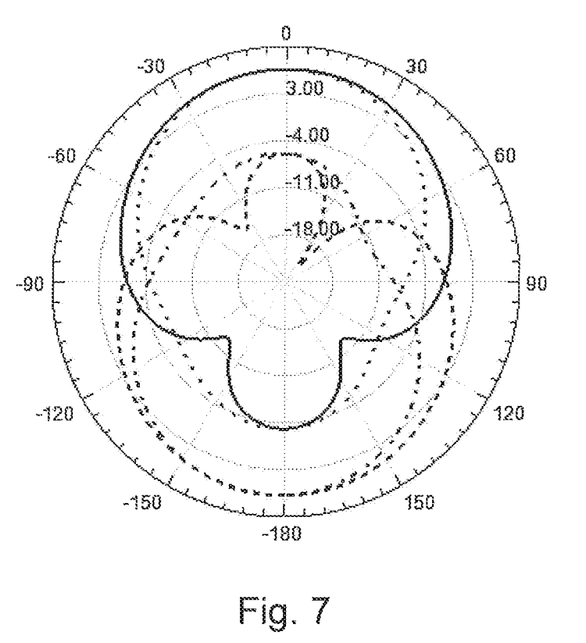
FIG. 7 shows 2D representations of the generated radiation patterns for the first and second slot antennas of FIG. 5.

FIG. 7 shows 2D representations of the generated radiation patterns at φ=0° and 90° while θ changes between −180 and 180, for the embodiment shown in FIG. 5. The radiation patterns are not distorted due to the fact that larger slots are edged on the backing surface of each slot.

Figure 8:
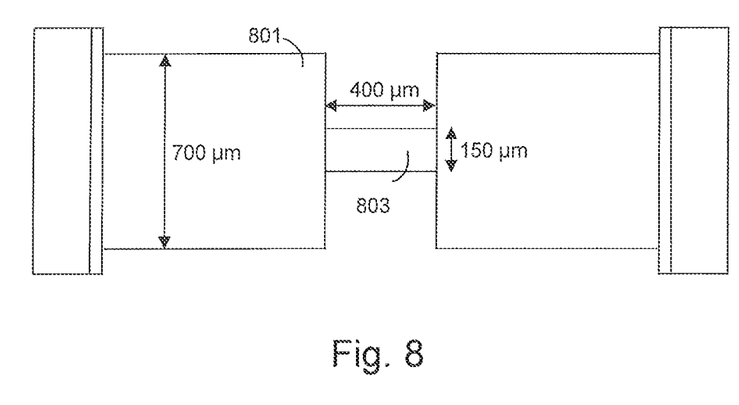
FIG. 8 shows a schematic of a switch used to switch a slot antenna between an active and inactive configuration in a relay device according to an embodiment.

In some embodiments, the switch(es) used to switch the first and second slot antennas between active and inactive configurations can be realized using RF-MEMS switches technology. The ON (active) state is simulated here by replacing the switch location with a conductive plane of width 150 μm and length 400 μm. The switch is positioned on a conductive bridge 801 as shown in FIG. 8. In the present embodiment, the width of the bridge is set to 700 μm (it will be understood that the precise length of the bridge will depend on the width of the slot). The OFF (inactive) state is simulated by an open circuit 803 of 400 μm between the bridge legs. The simulated performance results are not affected by the insertion of the additional switch model.

Figure 9:
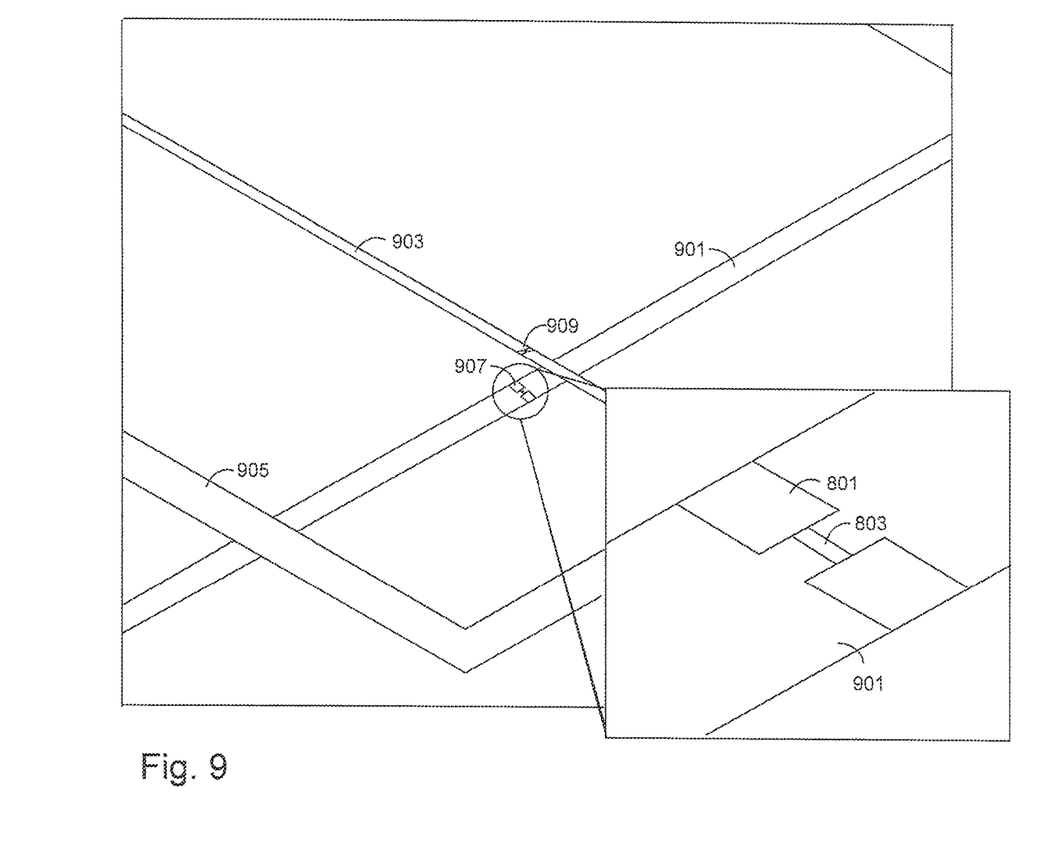
FIG. 9 shows a schematic of a relay device according to another embodiment.

FIG. 9 shows an example of how the switches may be positioned in the relay device. As in the embodiments described above, the relay device includes a first slot antenna and a second slot antenna, having respective slots 901, 903. A single stripline 905 is used to feed the two slot antennas. Each slot is provided with a switch 907, 909 that bridges the slot; as shown in the inset, the structure of the switches is the same as that shown in FIG. 8, with like parts being numbered with the same reference numerals.

While certain embodiments have been described, these embodiments have been presented by way of example only and are not intended to limit the scope of the invention. Indeed, the novel methods, devices and systems described herein may be embodied in a variety of forms; furthermore, various omissions, substitutions and changes in the form of the methods and systems described herein may be made without departing from the spirit of the invention. The accompanying claims and their equivalents are intended to cover such forms or modifications as would fall within the scope and spirit of the inventions.

The invention claimed is:

1. A relay device for relaying radio frequency signals received from an antenna implanted within a patient's body to another device located outside the patient's body, the relay device comprising:
   a first slot antenna for detecting radio frequency signals sent from the antenna implanted within the patient's body;
   a second slot antenna for transmitting radio frequency signals to said other device located outside the patient's body, the signals transmitted by the second slot antenna being used to relay information that is conveyed within the signals detected by the first slot antenna;
   wherein the first and second slot antennas comprise elongated slots on opposite sides of a cavity;
   the relay device comprising switching means for switching the first and second slot antennas between active and inactive configurations;
   wherein, when the first slot antenna is in its active configuration, the first slot antenna is operable to detect signals in a first frequency band of the first slot antenna and when the first slot antenna is in its inactive configuration, the first slot antenna is less responsive to detecting signals in the first frequency band of the first slot antenna compared to when the first slot antenna is in its active configuration; and
   when the second slot antenna is in its active configuration, the second slot antenna is operable to transmit signals in a first frequency band of the second slot antenna and when the second slot antenna is in its inactive configuration, the second slot antenna is less effective at transmitting signals in the first frequency band of the second slot antenna compared to when the second slot antenna is in its active configuration.

2. A relay device according to claim 1, wherein the switching means is configured such that when the first slot antenna is in its active configuration, the second slot antenna is in its inactive configuration and when the first slot antenna is in its inactive configuration, the second slot antenna is in its active configuration.

3. A relay device according to claim 2, wherein the switching means is configured to alternately activate the first and second slot antennas.

4. A relay device according to claim 1, wherein the switching means is configured to switch the first slot antenna from an active configuration to an inactive configuration by short circuiting the first slot antenna.

5. A relay device according to claim 4, wherein the switching means comprises a switch that bridges the sides of the first slot antenna and/or a switch that bridges the sides of the second slot antenna.

6. A relay device according to claim 5 wherein the switch(es) comprise RF-MEMS switches.

7. A relay device according to claim 1, wherein the switching means is configured to switch the second slot antenna from an active configuration to an inactive configuration by short circuiting the second slot antenna.

8. A relay device according to claim 1, wherein the slots in the first and second slot antennas are oriented such that they extend lengthwise in different directions from one another.

9. A relay device according to claim 8, wherein the slots of the first and second slot antennas extend lengthwise perpendicularly to one another.

10. A relay device according to claim 1, wherein the first and second slot antennas are both fed by a common feed.

11. A relay device according to claim 10, wherein the common feed is a stripline that passes through the cavity.

12. A relay device according to claim 1, wherein the slots in the first and second slot antennas widen as each slot extends lengthwise from its centre.

13. A relay device according to claim 12, wherein the width of the slots in the first and second slot antennas increases in a series of steps as each slot extends lengthwise from its centre.

14. A relay device according to claim 13, wherein at each step, the respective slot widens by a distance equivalent to the width of the slot at the mid-point along its length.

15. A relay device according to claim 14, wherein the relay device has means for attaching the device to the patient's skin.

16. A relay device according to claim 13, wherein the steps in the respective slots become progressively longer as each slot extends lengthwise from its centre.

17. A relay device according to claim 1, wherein the relay device is wearable by a patient.

* * * * *